United States Patent [19]

Witt et al.

[11] Patent Number: 5,093,325
[45] Date of Patent: Mar. 3, 1992

[54] COMBINATION PREPARATION HAVING ANTITHROMBOTIC ACTION

[75] Inventors: Werner Witt; Berthold Baldus; Bernd Müller; Claus-Steffen Stürzebecher; Werner Skuballa, all of Berlin, Fed. Rep. of Germany

[73] Assignee: Schering Aktiengesellschaft, Berlin and Bergkamen, Fed. Rep. of Germany

[21] Appl. No.: 591,108

[22] Filed: Oct. 1, 1990

[30] Foreign Application Priority Data

Sep. 29, 1989 [DE] Fed. Rep. of Germany ....... 3933027

[51] Int. Cl.$^5$ .................. A61K 31/19; A61K 31/045; A61K 31/60
[52] U.S. Cl. .................... 514/165; 514/573; 514/739; 514/822
[58] Field of Search ............... 514/165, 573, 739, 822

[56] References Cited

PUBLICATIONS

S. Stuerzebecher et al., "Platelet Inhibitory and Hemodynamic Effects of a New Stable PGI$_2$ Analogue, Cicaprost (ZK 96480), in Different Animal Species and in Man," Biomed. Biochim. Acta 47 (1988), 10/11, S45–S47.

Merck Index, Tenth Edition, p. 123, Aspirin.

Prostaglandins 36(6): 751–760, 1988, Stuerzebecher & Witt, The PGI$_2$-analog Iloprost and the TXA$_2$-receptor Antagonist Sulotroban Synergistically Inhibit TXAZ-dependent Platelet Activation.

Biomed. Biochim. Acta 47(10–11): 545–547, 1989, Stuerzebecher, Hildebrand, Schoebe, Seifert & Staks, Platelet Inhibitory and Hemodynamic Effects of a New Stable DGI$_2$ Analog, Cicaprost (ZK96480), in different animal species & man.

Primary Examiner—S. J. Friedman
Attorney, Agent, or Firm—Millen, White & Zelano

[57] ABSTRACT

The invention relates to a combination preparation for thrombosis treatment consisting of acetylsalicylic acid and carbacyclin derivatives.

21 Claims, No Drawings

COMBINATION PREPARATION HAVING ANTITHROMBOTIC ACTION

SUMMARY OF THE INVENTION

The invention relates to a combination product for inhibition of platelet function and for treatment of thrombosis containing the carbacyclin derivatives Cicaprost or Eptaloprost and acetylsalicylic acid (ASA, $CH_3-COO-C_6H_4-COOH$).

The activation of the platelets with subsequent aggregation plays a central role in arterial thrombogenesis and, with certain limitations, also in venous thrombogenesis. This platelet activation is caused by stimuli which can occur in a vascular trauma and coagulation activation, such as, e.g., by thrombin, collagen, adenosine diphosphate, adrenalin, or by the platelet-activating factor (PAF). These stimuli, besides the aggregation, at the same time cause the release of substances from the platelets, which are stored in the so-called granules of the platelets. Some of these substances, such as, e.g., plasminogen activator inhibitor 1 (PAI-1) or platelet-derived growth factor (PDGF), are probably particularly important for the pathogenesis of thrombotic/atherosclerotic diseases.

Thus, PAI-1 is a potent inhibitor of plasminogen activators, such as urokinase and t-PA (tissue plasminogen activator), and by this property inhibits fibrinolysis, which is necessary for reestablishment of the blood flow after thrombotic occlusion. PDGF is a mitogen which stimulates the proliferation of different cell types (especially smooth muscle cells). Because of this mechanism, a key role is ascribed to PDGF in atherogenesis. The inhibition not only of the aggregation of platelets but also of the release of pathogenic substances, such as PAI-1 and PDGF, could make an important contribution to the prophylaxis of thromboembolic and atherosclerotic diseases.

Acetylsalicylic acid, a known platelet aggregation inhibitor, is only a weak inhibitor of the platelet function and also only a weak antithrombotic agent. As a cyclooxygenase inhibitor, acetylsalicylic acid inhibits only one form of platelet activation, the thromboxane formation. In addition, acetylsalicylic acid in the vascular endothelium will inhibit the formation of prostacyclin, a natural platelet inhibitor. Therefore, the therapeutic effective strength of acetylsalicylic acid for treatment of many thromboembolic forms of diseases is not sufficient.

Mimetics of natural prostacyclin, such as said carbacyclin derivatives, have been available quite recently for clinical use in oral form. They are regarded as inhibitors of all essential ways of activation of platelets and strong platelets inhibitors and antithrombotic agents. In addition, they have other properties, such as, e.g., the capability for relaxation of smooth vascular muscles, which support their therapeutic action in certain forms of disease. In high dosages, the characteristic side effect profile for the substance class of carbacyclins comes to the fore, as a result of which the usable maximum dose is limited, and limits are set to the full clinical use of the platelet function inhibition action and the antithrombotic action.

It has now been surprisingly found that combination preparations of Cicaprost and acetylsalicylic acid and of Eptaloprost and acetylsalicylic acid act synergistically in various biological systems, e.g., human and other mammals, or show cooperative effects of the individual active ingredients.

Both combinations exceed, e.g., the antithrombotic strength of acetylsalicylic acid, and allow a considerable dose reduction for the platelet-inhibiting carbacyclin portion in comparison with equipotent dosages of the carbacyclin (Cicaprost, Eptaloprost) administered alone by a factor up to 10.

Thus, the combinations are stronger platelet inhibitors and stronger antithrombotic agents than acetylsalicylic acid with a higher specificity and therapeutic breadth in comparison to Cicaprost/ Eptaloprost by cooperative strengthening of their thrombotic active ingredients. Furthermore, the undesirable gastrointestinal side effects produced by acetylsalicylic acid are reduced by the gastroprotective properties of the carbacyclin.

Thus, the invention relates to a combination preparation containing acetylsalicylic acid and Cicaprost or Eptaloprost, and the carbacyclins also can be used in the form of their addition salts with physiologically compatible bases or their clathrates with cyclodextrins, as well as pharmaceutical agents with the usual auxiliary agents and vehicles for inhibition of the platelet function and for thrombosis treatment.

Eptaloprost [(5E)-(16S)-13,14-didehydro-1a,1b-dihomo-16,20-dimethyl-3-oxa-18,18,19,19-tetradehydro-6a-carbaprostaglandin-$I_2$] and its $\beta$-cyclodextrin clathrate can be prepared according to the following formula:

17.2 ml of a 50% sodium hydroxide solution and 337 mg of tetrabutyl ammonium hydrogen sulfate are added to a mixture of 6.9 g of 2-[(E)-(1S,5S,6S,7R)-7-(dimethyl-tert.-butylsilyloxy)-6-[(3S,4S)-3-(dimethyl)-tert.-butylsilyloxy)-4-methyl-nona-1,6-diinyl]-bicyclo[3.3.-0]octan-3-ylidene]-ethan-1-ol (W. Skuballa, E. Schillinger, C.S. Strzebecher, M. Vorbrugger, J. Medicinal Chemistry 29 313 (1986); described therein as compound 15a) and 11.5 g of trimethyl-ortho-4-bromobutyrate and stirred for 16 hours at 22° C. under argon. Then with ice cooling, it is diluted with 20 ml of water and acidified with 10% citric acid solution to pH 5. It is extracted three times, in each case with 300 ml of ether. The organic phase is washed once with 200 ml of brine, dried on magnesium sulfate, and concentrated by evaporation in a vacuum. After chromatography of the residue on silica gel with hexane/ether (8+2), 7.6 g of (5E)-(16S)-13,14-didehydro-1a,1b-dihomo-16,20-dimethyl-3-oxa-18,18,19,19-tetradehydro-6a-carbaprostaglandin-$I_2$-methylester -11,15-bis(dimethyl-tert.-butyl-ether) is obtained as colorless oil.

IR ($CHCl_3$) 2953, 2925, 2859, 2230, 1730, 1250, 838 $cm^{-1}$.

For silyl ether cleavage, 7.25 g of the abovedescribed bissislyl ether is stirred for 48 hours at 24° C. with 600 ml of a mixture of acetic acid/water/tetrahydrofuran (65+35+10). Then it is concentrated by evaporation in a vacuum, and the residue is chromatographed on silica gel. With ethyl acetate/hexane (3+2), 3.9 g of (5E)-(16S)-13,14-didehydro-1a,1b-dihomo-16 -dimethyl-3-oxa -18,18,19,19-tetradehydro-6a-carboprostaglandin-$I_2$-methylester is obtained as colorless oil.

IR ($CHCl_3$) 3400 (broad), 2935, 2865, 2230, 1735 $cm^{-1}$.

For saponification, a solution of 3.66 g of the above-produced methylether is stirred in 35 ml of methanol with 35 ml of a 0.5 molar sodium hydroxide solution for 30 minutes at 24° C. under argon. Then it is diluted with 20 ml of water, acidified with a 20% citric acid to pH 2, and extracted four times, each time with 100 ml of methylene chloride. The organic phase is washed once with 50 ml of brine, dried on sodium sulfate, and concentrated by evaporation in a vacuum. The residue is chromatographed with ethyl acetate on silica gel. Thus, 3.4 g of the title compound is obtained as colorless oil.

IR (CHCl$_3$): 3400 (broad), 2962, 2940, 2865, 2230, 1722 cm$^{-1}$.

β-cyclodextrin clathrate of (5E)-(16S)-13, 14-didehydro-1a,1b-dihomo-16,20-dimethyl-3-oxa -18,18,19-tetradehydro-6a-carbaprostaglandin-I$_2$:

41.75 g of β-cyclodextrin is dissolved in 298 ml of water at 80° C. and a solution of 1.5 g of (5E)-(16S)-13,14-didehydro-1a,1b -dihomo-16,20-dimethyl -3-oxa-18,18,19,19-tetradehydro-6a-carbaprostaglandin-I$_2$ in 24 ml of ethanol is instilled in 15 minutes. It is stirred for 4 hours at 60° C. and then allowed to cool overnight with stirring. The precipitated solid is suctioned off, washed with 50 ml of a mixture of water-ethanol (1:1), and dried for 24 hours at 0.1 torr and 25° C. on phosphorus pentaoxide. 38 g of free-flowing crystals of the β-analog cyclodextrin clathrate of the above-mentioned carbacyclin analog is obtained. The content of carbacyclin analogs in the clathrate is determined by titration and amounts to 3.3%.

Cicaprost, [2-[2E, 3aS, 4S, 5R, 6aS)-hexahydro-5-hydroxy-4-[(3S,4S) -3-hydroxy-4-methyl-1,6-nonadiynyl]-2(1H)-pentalenylidene]ethoxy] acetic acid, and its β-cyclodextrin clathrate can be produced according to the processes described in EP-PS 119,949 and in International Laid-Open Specification WO 87/05294.

Inorganic and organic bases suitable for formation of physiologically compatible salts are known to one skilled in the art. There can be mentioned, for example, alkali hydroxides, such as sodium and potassium hydroxide, alkaline-earth hydroxides such as calcium hydroxide, ammonia, amines, such as ethanolamine, diethanolamine, triethanolamine, N-methylglucamine, morpholine, tris-(hydroxymethyl)-methylamine, etc.

The cyclodextrin employed for the clathrate formation is preferably β-cyclodextrin.

The compounds of this invention can be employed in mixture with conventional excipients, i.e., pharmaceutically acceptable organic or inorganic carrier substances suitable for parenteral, enteral, or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring, and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir, or the like can be used wherein a sweetened vehicle is employed. Sustained release compositions can be formulated, including those wherein the active compound is protected with differentially degradable coatings, e.g., by microencapsulation, multiple coatings, etc.

ASA and the carbacyclin derivative can be administered in the same or in separate dosage units. In the case of separate dosage units, the dosage units can be administered sequentially, in either order, or simultaneously.

Acetylsalicylic acid and said carbacyclins are used in amounts that are below the otherwise usual amounts for the individual substances of the combination. The amounts to be used according to this invention will depend on the extent of the thrombosis.

Typically, acetylsalicylic acid is administered, as an individual substance, in an amount of 50–500 mg/patient/day; and Cicaprost is typically administered, as an individual substance, in an amount of 1.5–15 μg/patient/day. Bioequivalent amounts of Eptaloprost can be routinely determined by one skilled in the art using known protocols.

The combination according to the invention is preferably administered orally. Acetylsalicylic acid and Carbacyclin are in a weight ratio of $5 \times 10^{-6}$: 1 to 1:1, and a Carbacyclin dosage unit is 1–1000 micrograms, and in acetylsalicyclic acid dosage unit is 1–500 mg.

The combination according to the invention is preferably administered orally. Acetylsalicylic acid and carbacyclin are used in a weight ratio of about 1:5-10$^{-6}$-1:1. The Cicaprost dosage unit is about 0.5–10 μg/patient/day, preferably 0.5–5 μg/patient/day. Here, again, bioequivalent amounts of Eptaloprost can readily be determined by one skilled in the art using known protocols. The acetylsalicylic acid dosage unit is about 10–150 mg/patient/day.

It will be appreciated that the actual amounts of active compounds used will vary according to the specific compounds being utilized, the particular compositions formulated, the mode of application, and the particular situs and organism being treated. Optimum application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited above and below, and of corresponding West German Application P 39 33 027.3, filed Sept. 29, 1989, are hereby incorporated by reference.

EXAMPLES

Example 1

Human platelet-rich plasma (PRP) is incubated in an aggregometer at 37° C. and mixed with 3 ng/ml of collagen to cause aggregation. Cicaprost and ASA, as well as combinations of the two substances, are pipetted for 1 minute before addition of the activator collagen to the batch. The course of the aggregation is recorded in the aggregometer. 10 minutes after collagen addition, the samples are centrifuged at 3000 rpm and the supernatant is tested with an enzyme linked immunosorbent assay (ELISA) for its content of plasminogen activator inhibitor-1 (PAI-1) and with a radioimmunoassay (RIA) for the content of platelet-derived growth factor (PDGF).

Results

The separately ineffective concentrations of $10^{-10}$ or $10^{-9}$ M Cicaprost when combined with the also ineffective or slightly effective concentrations of $3 \times 10^{-5}$, $10^{-4}$ and $3 \times 10^{-4}$ M ASA lead to platelet aggregation inhibitions of 42%, 71% and 91% (see Table 1). The production of PAI-1 at the same inhibitor concentrations is inhibited 36%, 54% and 64%, and the release of PDGF is inhibited 24%, 42% and 55%. The action of the Cicaprost/ASA combinations is synergistic according to the definition of M.C. Berenbaum (Clin. exp. Immunol. 28:1–17, 1977).

TABLE 1

Inhibition of aggregation as well as PAI-1 and PDGF Release of human platelets stimulated with collagen in % of the control reaction (N = 6 = number of test samples)

| | | % INHIBITION | | |
|---|---|---|---|---|
| | | Aggregation | PAI-1 | PDGF |
| Cicaprost | $10^{-10}$M | 4 ± 3 | 0 ± 8 | 1 ± 2 |
| | $10^{-9}$M | 0 ± 3 | 0 ± 12 | 3 ± 3 |
| | $10^{-8}$M | 95 ± 4 | 72 ± 3 | 81 ± 3 |
| | $10^{-7}$M | 95 ± 3 | 80 ± 5 | 81 ± 1 |
| ASA | $3 \times 10^{-5}$M | 2 ± 1 | 6 ± 10 | 8 ± 2 |
| | $10^{-4}$M | 9 ± 3 | 10 ± 8 | 26 ± 6 |
| | $3 \times 10^{-4}$M | 30 ± 6 | 28 ± 4 | 39 ± 2 |
| | $10^{-3}$M | 46 ± 6 | 27 ± 10 | 47 ± 4 |
| Cicaprost + ASA | $10^{-10}$M $3 \times 10^{-5}$M | 42[a] ± 17 | 36 ± 14 | 24 ± 10 |
| Cicaprost + ASA | $10^{-9}$M $10^{-4}$M | 71[a] ± 12 | 54[a] ± 9 | 42 ± 8 |
| Cicaprost + ASA | $10^{-9}$M $3 \times 10^{-4}$M | 91[a] ± 2 | 64[a] ± 5 | 55[a] ± 6 |

[a]significant in comparison with ASA and Cicaprost individual doses (= 5% rank sum test)

Example 2

Reversible thrombocytopenias are produced on anesthetized guinea pigs by injection of collagen (40 g/kg i.v.). The cause of these thrombocytopenias is an aggregate formation of the collagen-stimulated blood platelets and the embolization of these platelet aggregates in the lungs, where they then lodge and thus cause the observed drops of the platelet count in the blood (thrombocytopenias). The thrombocytopenias, constant under control conditions (average 40% drops of the platelet count from the respective basal level), serve as a measurement of the intravascular platelet aggregation.

Results

The separately ineffective dose of 1 ng/kg/min i.v. of Cicaprost when combined with the weakly inhibiting dose of 0.5 mg/kg i.v. of ASA leads to a thrombocytopenia inhibition of 34%, significant in comparison with the control and the respective individual doses of the two active ingredients (see Table 2). Otherwise, this effect is achieved only by a three-fold higher dose of Cicaprost.

TABLE 2

Inhibition of collagen-induced thrombocytopenia on guinea pig (average value ± SEM).

| | | N | % Thrombocytopenia Inhibition |
|---|---|---|---|
| Control | | 8 | 2 ± 6 |
| Cicaprost | 1 ng/kg/min | 6 | 8 ± 5[n.s.] |
| | 3 ng/kg/min | 6 | 36 ± 4[a] |
| ASA | 0.5 mg/kg | 8 | 17 ± 3[a] |
| ASA Cicaprost | 0.5 mg/kg + 1 ng/kg/min | 8 | 34 ± 5[a,b] |

[a]significant in comparison with control (t-test, p less than 0.05)
[b]significant in comparison with ASA/Cicaprost (p less than 0.01)
[n.s.]not significant

Example 3

A mesenteric loop is placed on an anesthetized guinea pig and is superfused with a moderately heated solution of common salt. Under intravital microscopic control the vascular wall of a mesenteric arteriole (020–50 m) is traumatized by a series of electric pulses. By subsequent local application of increasing concentrations of ADP (adenosine diphosphate) solution a thrombogenic ADP concentration is determined, at which an occluding platelet thrombus forms on the pretraumatized site of the arteriole. This thrombogenic ADP concentration produces vascular-specific and reproducible thrombi in the respective arteriole.

Results

ASA 10 mg/kg i.v. does not change the thrombogenic ADP concentration (see Table 3). Cicaprost 10 ng/kg/min i.v. is not significantly effective either. The combination of these doses of Cicaprost and ASA, ineffective on this thrombosis model, leads to a significant increase of the thrombogenic ADP concentration by $1.27 + 0.54$ log M (=the 30.9-fold of the starting concentration). This antithrombotic action of the combination cannot be achieved by ASA alone and can be achieved by Cicaprost individual doses only in a 10-fold higher dosage (100 ng/kg/min i.v.: increase by $1.32 \pm 0.2$ log M ADP, N=5).

TABLE 3

Action of Cicaprost, ASA and a combination of Cicaprost + ASA on the development of occluding platelet thrombi on previously traumatized mesenteric arterioles of the guinea pig (average values ± SEM).

| | | Thrombogenic ADP Concentration | | |
|---|---|---|---|---|
| | | N | Starting value | Increase |
| Cicaprost | 10 ng/kg/min | 5 | 84.6 ± 54.9 + 0.36[n.s.] | ±0.39 |
| | 30 ng/kg/min | 5 | 79.8 ± 29.6 + 1.02[a] | ±0.20 |
| | 100 ng/kg/min | 5 | 64.6 ± 23.7 + 1.32[a] | ±0.20 |
| ASA | 10 mg/kg | 5 | 26.1 ± 13.9 + 0.06[n.s.] | ±0.13 |
| Cicaprost + | 10 ng/kg/min | | | |
| ASA | 10 mg/kg | 5 | 13.8 ± 6.7 + 1.27[a,b] | ±0.54 |

[a]significant in comparison with control (t-test, p less than 0.05)
[b]significant in comparison with ASA/Cicaprost individual doses (p less than 0.05)
[n.s.]not significant

Example 4

A 2-cm-long piece of the external left carotid artery on an anesthetized guinea pig is carefully exposed and drawn over a small metal plate. Then the vascular wall is weighted down over a length of 1 cm for 3 minutes with a steel stamp weighing 200 g, cooled to −15° C. In this way, a massive local vascular trauma is caused on a large artery and a red thrombus develops on the traumatized site. Three hours after the trauma the traumatized segment and an equally long piece of the contralateral artery are removed, asked and put in hemoglobin test reagent. The hemoglobin contents of the two segments are determined 24 hours later. The net hemoglobin content of the red thrombus as the measurement of the thrombus size is calculated from the difference of these hemoglobin contents.

Results

ASA 5 mg/kg i.v. has no significant effect on the thrombus formation in the carotid artery of the guinea pig (see Table 4). micaprost in the also significantly effective dosage of C.3 ng/kg/min i.v. leads, in combination with ASA, to a significant antithrombotic action: the thrombus-hemoglobin content is reduced by 85%, in comparison with the control, from 8.6 micromol (median) to 1.3 micromol.

TABLE 4

Action of Cicaprost, ASA and a combination of Cicaprost + ASA on the thrombus formation in carotid arteries of guinea pigs previously traumatized by pressure + cold (median and quartiles of the thrombus-hemoglobin[Hb] contents).

|  |  | N | Thrombus Hb content [$^4$mol] | |
|---|---|---|---|---|
|  |  |  | Median | Q 25/Q 75 |
| Control |  | 30 | 8.6 | 5.7/12.1 |
| Cicaprost | 0.3 ng/kg/min | 10 | 12.4$^{n.s}$ | 8.0/25.0 |
|  | 1.0 ng/kg/min | 10 | 1.9$^a$ | 0.2/5.8 |
|  | 3.0 ng/kg/min | 11 | 0$^a$ | −0.4/0.7 |
| ASA | 5 mg/kg | 10 | 3.4$^{n.s.}$ | −0.1/13.8 |
| Cicaprost + ASA | 0.3 ng/kg/min 5 mg/kg | 10 | 1.3$^{a,b}$ | −1.2/5.1 |

$^a$significant in comparison with control ( = 5%, rank sum test)
$^b$significant in comparison with Cicaprost
$^{n.s}$insignificant

What is claimed is:

1. A pharmaceutical composition suitable for inhibition of platelet function and for thrombosis treatment comprising acetylsalicyclic acid and a carbacyclin derivative, wherein said carbacyclin derivative is Cicaprost, Eptaloprost or pharmaceutically acceptable salts or clathrates thereof and wherein acetylsalicylic acid and said carbacyclin derivative are present in a weight ratio of about $1:5 \times 10^{-4} - 1:1$.

2. A composition according to claim 1, wherein said carbacyclin derivative is present in an amount of about 0.5–10 μg/day and acetylsalicyclic acid is present in an amount of about 10–150 mg/day.

3. A composition according to claim 1, wherein said carbacyclin derivative is Cicaprost, a pharmaceutically acceptable salt thereof or a pharmaceutically acceptable clathrate thereof.

4. A composition according to claim 1, wherein said carbacyclin derivative is Eptaloprost, a pharmaceutically acceptable salt thereof or a pharmaceutically acceptable clathrate thereof.

5. A composition according to claim 1, wherein said carbacyclin derivative is Cicaprost.

6. A composition according to claim 1, wherein said carbacyclin derivative is Eptaloprost.

7. A composition according to claim 1, wherein said carbacyclin derivative is β-cyclodextrin clathrate of Cicaprost.

8. A composition according to claim 1, wherein said carbacyclin derivative is β-cyclodextrin clathrate of Eptaloprost.

9. A composition according to claim 1, wherein said composition is suitable for oral administration.

10. A composition according to claim 1, wherein said composition is suitable for administration to humans.

11. A composition according to claim 1, wherein said composition is in the form of a kit containing separate dosage units of acetysalicylic acid and said carbacyclin derivative.

12. A method for inhibiting platelet function or treatment of thrombosis comprising administering a composition according to claim 1.

13. A method according to claim 12, wherein acetylsalicylic acid and said carbacyclin derivative are present in a weight ratio of about $1:5-10^{-6}1:1$.

14. A method according to claim 12, wherein said carbacyclin derivative is present in an amount of 0.5–10 μg/day and acetylsalicylic acid is present in an amount of about 10–150 mg/day.

15. A method according to claim 12, wherein said carbacyclin derivative is Cicaprost, a pharmaceutically acceptable salt thereof or a pharmaceutically acceptable clathrate thereof.

16. A method according to claim 12, wherein said composition is administered orally.

17. A method for inhibiting platelet function or treatment comprising separately administering acetylsalicylic acid and a carbacyclin derivative, wherein said carbacyclin derivative is Cicaprost, Eptaloprost or pharmaceutically acceptable salts or clathrates thereof.

18. A method according to claim 17, wherein acetylsalicylic acid and said carbacyclin derivative are administered in a weight ratio of about $1:5-10^{-6}1:1$.

19. A method according to claim 17, wherein acetylsalicylic acid as administered in a dosage unit of about 10–150 mg/day and said carbacyclin derivative is administered in a dosage unit of about 0.5–10 μg/day.

20. A method according to claim 17, wherein said composition is administered orally.

21. A pharmaceutical composition according to claim 1, wherein the dosage of said carbacyclin derivative is 1–1000 micrograms and the dosage of said acetylealicylic acid is 1–500 mg.

* * * * *